United States Patent [19]
Jackson et al.

[11] Patent Number: 5,643,240
[45] Date of Patent: Jul. 1, 1997

[54] APERTURED FILM/NONWOVEN COMPOSITE FOR PERSONAL CARE ABSORBENT ARTICLES AND THE LIKE

[75] Inventors: Wanda Walton Jackson, Alpharetta; Monica Signoret Diaz, Woodstock; Cheryl Anne Perkins, Roswell, all of Ga.; Dawn Marie Huffman, Neenah, Wis.; Wendy Louise Bush, Maidstone, England; Cheryl Ann Mocadlo, New London, Wis.; Richard John Birtwell, Maidstone, England

[73] Assignee: Kimberly-Clark Corporation, Neenan, Wis.

[21] Appl. No.: 665,710

[22] Filed: Jun. 18, 1996

Related U.S. Application Data

[63] Continuation of Ser. No. 484,368, Jun. 7, 1995, abandoned, which is a continuation of Ser. No. 175,652, Dec. 30, 1993, abandoned.

[51] Int. Cl.$^6$ .............................. A61F 13/15; A61F 13/20
[52] U.S. Cl. ........................ 604/378; 604/366; 604/370; 604/383
[58] Field of Search .................... 604/358, 366–367, 604/370, 378, 383–384, 385.1

[56] References Cited

U.S. PATENT DOCUMENTS

| | | |
|---|---|---|
| 2,908,064 | 10/1959 | Lauterbach et al. . |
| 3,276,944 | 10/1966 | Levy . |
| 3,307,545 | 3/1967 | Surowitz . |
| 3,338,992 | 8/1967 | Kinney . |
| 3,341,394 | 9/1967 | Kinney . |
| 3,423,266 | 1/1969 | Davies et al. . |
| 3,502,538 | 3/1970 | Petersen . |
| 3,502,763 | 3/1970 | Hartmann . |
| 3,542,615 | 11/1970 | Dobo et al. . |
| 3,692,618 | 9/1972 | Dorschner et al. . |
| 3,802,817 | 4/1974 | Matsuki et al. . |
| 3,849,241 | 11/1974 | Butin et al. . |
| 3,929,135 | 12/1975 | Thompson . |
| 3,967,623 | 7/1976 | Butterworth et al. . |
| 3,994,299 | 11/1976 | Karami . |

(List continued on next page.)

FOREIGN PATENT DOCUMENTS

| | | |
|---|---|---|
| 803714 | 1/1969 | Canada . |
| 0018020 | 10/1980 | European Pat. Off. . |
| 0039974 | 11/1981 | European Pat. Off. . |
| 0059506 | 9/1982 | European Pat. Off. . |
| 0084456 | 7/1983 | European Pat. Off. . |
| 0168225 | 1/1986 | European Pat. Off. . |
| 0172420 | 2/1986 | European Pat. Off. . |
| 0203823 | 12/1986 | European Pat. Off. . |
| 0237990 | 9/1987 | European Pat. Off. . |
| 0248598 | 12/1987 | European Pat. Off. . |
| 0260974 | 3/1988 | European Pat. Off. . |
| 0360929 | 4/1990 | European Pat. Off. . |

(List continued on next page.)

OTHER PUBLICATIONS

International Search Report for International Application No. PCT/US/14937, dated Jun. 26, 1995.
French Search Report for French Patent Application No. 0 509 488 dated Jun. 21, 1995.
NRL Report 4364, "Manufacture of Super–Fine Organic Fibers" by V. A. Wendt, E. L. Boone and C. D. Fluharty May 25, 1954.
NRL Report 5265, "An Improved Device For The Formation of Super–Fine Thermoplastic Fibers" by K. D. Lawrence, R. T. Lukas and J. A. Young, Feb. 1959.

*Primary Examiner*—John G. Weiss
*Assistant Examiner*—P. Zuttarelli
*Attorney, Agent, or Firm*—Patrick C. Wilson

[57] ABSTRACT

Disclosed herein is a combination apertured film and lofty fibrous nonwoven web separation layer which is particularly well suited for use as, among other things, a body side liner for personal care absorbent articles such as sanitary napkins and the like. When used in such applications, the material of the present invention has excellent liquid penetration rates and it resists rewet of the surface of the material.

17 Claims, 1 Drawing Sheet

U.S. PATENT DOCUMENTS

| | | | |
|---|---|---|---|
| 4,321,924 | 3/1982 | Ahr . | |
| 4,324,246 | 4/1982 | Mullane et al. . | |
| 4,327,730 | 5/1982 | Sorensen . | |
| 4,340,563 | 7/1982 | Appel et al. . | |
| 4,342,314 | 8/1982 | Radel et al. . | |
| 4,362,777 | 12/1982 | Miller . | |
| 4,463,045 | 7/1984 | Ahr et al. . | |
| 4,551,378 | 11/1985 | Carey, Jr. . | |
| 4,629,643 | 12/1986 | Curro et al. . | |
| 4,668,566 | 5/1987 | Braun . | |
| 4,690,679 | 9/1987 | Mattingly, III et al. . | |
| 4,710,186 | 12/1987 | DeRossett et al. . | |
| 4,801,494 | 1/1989 | Datta et al. . | |
| 4,806,411 | 2/1989 | Mattingly, III et al. . | |
| 4,814,032 | 3/1989 | Taniguchi et al. . | |
| 4,883,707 | 11/1989 | Newkirk | 604/370 |
| 4,902,553 | 2/1990 | Hwang et al. . | |
| 4,908,026 | 3/1990 | Sukiennik et al. | 604/378 |
| 4,916,005 | 4/1990 | Lippert et al. . | |
| 5,009,650 | 4/1991 | Bernardin | 604/378 |
| 5,037,409 | 8/1991 | Chen et al. | 604/358 |
| 5,068,141 | 11/1991 | Kubo et al. . | |
| 5,078,710 | 1/1992 | Suda et al. | 604/366 |
| 5,089,075 | 2/1992 | Sonoda . | |
| 5,108,827 | 4/1992 | Gessner . | |
| 5,130,196 | 7/1992 | Nishio et al. . | |
| 5,133,917 | 7/1992 | Jezic et al. . | |
| 5,135,521 | 8/1992 | Luceri et al. . | |
| 5,188,625 | 2/1993 | Van Iten et al. . | |
| 5,248,309 | 9/1993 | Serbiak et al. . | |
| 5,264,268 | 11/1993 | Luceri et al. . | |
| 5,356,405 | 10/1994 | Thompson et al. | 604/358 |
| 5,383,870 | 1/1995 | Takai et al. | 604/366 |
| 5,387,209 | 2/1995 | Yamamoto et al. | 604/358 |

FOREIGN PATENT DOCUMENTS

| | | |
|---|---|---|
| 0394954 | 10/1990 | European Pat. Off. . |
| 0421734 | 4/1991 | European Pat. Off. . |
| 0269051 | 11/1992 | European Pat. Off. . |
| 0523683 | 1/1993 | European Pat. Off. . |
| 0532005 | 3/1993 | European Pat. Off. . |
| 0539703 | 5/1993 | European Pat. Off. . |
| 1526778 | 9/1978 | United Kingdom . |
| 1540474 | 2/1979 | United Kingdom . |
| 2115343 | 9/1983 | United Kingdom . |
| 2125458 | 3/1984 | United Kingdom . |
| 2243283 | 10/1991 | United Kingdom . |
| 93/09744 | 5/1993 | WIPO . |
| WO93/09741 | 5/1993 | WIPO . |
| WO93/11725 | 6/1993 | WIPO . |
| 94/28838 | 12/1994 | WIPO . |

APERTURED FILM/NONWOVEN COMPOSITE FOR PERSONAL CARE ABSORBENT ARTICLES AND THE LIKE

This application is a continuation of application Ser. No. 08/484,368 entitled "APERTURED FILM/NONWOVEN COMPOSITE FOR PERSONAL CARE ABSORBENT ARTICLES AND THE LIKE" and filed in the U.S. Patent and Trademark Office on Jun. 7, 1995 now abandoned, which is a continuation of application Ser. No. 08/175,652 entitled "APERTURED FILM/NONWOVEN COMPOSITE FOR PERSONAL CARE ABSORBENT ARTICLES AND THE LIKE" and filed in the U.S. Patent and Trademark Office on Dec. 30, 1993, now abandoned. The entirety of this application is hereby incorporated by reference.

FIELD OF THE INVENTION

The present invention is directed to a combination apertured film and lofty fibrous nonwoven material. The material as described herein is particularly well-suited for use as a cover material for personal care absorbent articles including, but not limited to, sanitary napkins.

BACKGROUND OF THE INVENTION

The purpose of personal care absorbent articles including sanitary napkins or feminine pads, diapers, incontinence garments, training pants, bandages and the like is to absorb and contain body exudates including blood, menses, urine and feces. Personal care absorbent articles typically include a body side liner adapted to be placed adjacent to the wearer's skin, a back side layer or baffle which is usually liquid impervious to retain the exuded body fluids and an absorbent core whose purpose it is to store the exuded body fluids. Whether or not a particular personal care absorbent article will work well is a function of the interaction between all the components of the particular article. Two of the most important parameters for such articles are fluid intake time and fluid rewet. To be effective, personal care absorbent articles must take in exuded body fluids as quickly as possible. Once the body fluids have been taken in, it is desirable that the fluids not flow back towards and rewet the body side surface of the personal care absorbent article. By increasing the rate at which a fluid is taken into an absorbent article and by reducing the amount of rewet of that fluid to the body side surface, the article will typically have a cleaner and drier surface and, thus, will be more aesthetically pleasing and functionally acceptable to the end-user.

Feminine hygiene products including feminine pads or sanitary napkins are at a particular disadvantage from the standpoint of providing fast penetration rates and low rewet characteristics due to the nature of the exudated body fluid. Menses, as compared to urine, is a very viscous material. As a result, any tendencies by the sanitary napkin to have poor intake rates and high rewet characteristics are exacerbated by the properties of the fluid itself.

Apertured films and fibrous nonwoven webs are two materials used to form the body side liner of personal care absorbent articles and sanitary napkins in particular. Both of these materials have been used alone or in combination as the body contacting surface or layer in such products. Apertured films, by themselves, unless highly engineered, are two-dimensional in nature and while providing a non-staining surface, do not typically function well at preventing rewet. Lofty fibrous nonwoven web covers allow rapid penetration of fluid and help provide separation from the fluid, but the same materials can retain some of the fluid within their structure adjacent the top surface thereby resulting in a wet feeling and an obvious stain problem. This wet feeling and staining is undesirable for many users. Another problem with fibrous nonwoven web cover materials is the balancing of abrasion resistance with softness. More lofty materials tend to provide a softer feel and better fluid intake rate but the same materials also suffer from poor abrasion resistance. Conversely, more densified and therefore more abrasion-resistant materials tend to hold up better during use but also provide less desirable fluid intake rates. Combinations of films and fibrous nonwoven webs have been attempted but, again, due to the extreme variance in materials and properties as well as their interactive characteristics, the resultant products have met with varying degrees of success. There is therefore a need for an improved material which can be utilized for, among other things, a body side liner or cover material for personal care absorbent products.

SUMMARY OF THE INVENTION

The present invention is directed to a combination apertured film and lofty fibrous nonwoven web separation material which is particularly well suited for use as a cover material for personal care absorbent articles including, but not limited to, sanitary napkins. Personal care absorbent articles, including sanitary napkins, diapers, training pants, incontinence garments, bandages and the like typically include a bodyside liner or cover adapted to be worn adjacent the wearer's skin and a backside liner which is typically designed to retain any exuded body fluids. Disposed between the bodyside liner and the backside liner is an absorbent core. In some constructions, the bodyside liner is wrapped around the entire product including the backside liner while in other configurations, the bodyside liner is sealed to the backside liner around the periphery of the overall product to form a chamber which houses the absorbent core. The material of the present invention includes an apertured film layer and a separation layer with the combination being usable as a bodyside liner for such personal care absorbent articles. The film layer defines a plurality of apertures therein which collectively have a percent open area between about 10% and 30%. The separation layer comprises a fibrous nonwoven web having a bulk between about 0.76 and 3.8 millimeters, a basis weight of between about 17 and 85 grams per square meter, and an average pore size of between about 100 and 400 microns. An important parameter of the present invention is that the fibrous nonwoven web separation layer be lofty in nature so as to allow the combination aperture film and separation layer to have good penetration rates for absorbed body fluids and low re-wet values so that the fluid, once absorbed, does not flow back to the surface of the product. To this end, it is advantageous to use bicomponent fibers in forming the fibrous nonwoven web separation layer. Such bicomponent fibers come in a wide variety of configurations including, but not limited to, side-by-side and sheath-core fiber configurations. Suitable polymers for such bicomponent fibers include, but are not limited to, polyesters and polyolefins such as polyethylene and polypropylene. Suitable fiber deniers would typically range between about 1.5 and 6.

DETAILED DESCRIPTION OF THE INVENTION

Figure 1:
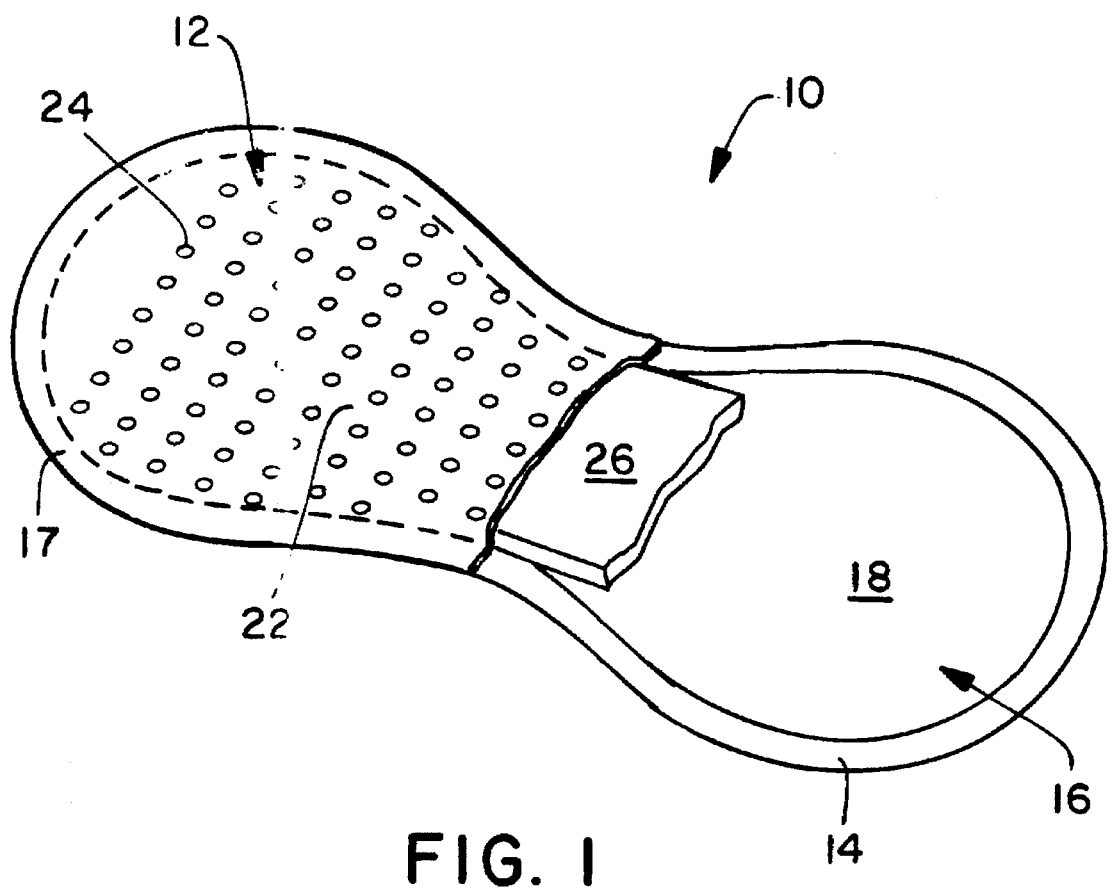
FIG. 1 is a partial cut away perspective view of a personal care absorbent article according to the present invention, in this case a sanitary napkin, employing a combined film and lofty nonwoven material according to the present invention as the cover material for the sanitary napkin.
Figure 2:
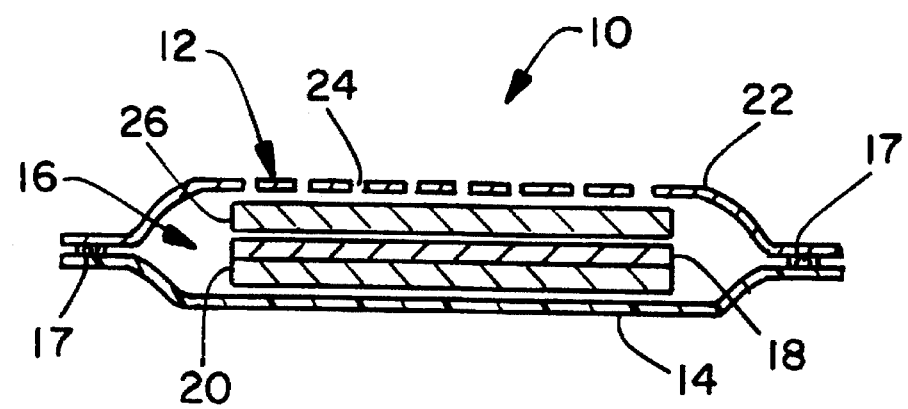
FIG. 2 is a cross-sectional side view of a personal care absorbent article according to the present invention such as is shown in FIG. 1 of the drawings.

Referring to FIGS. 1 and 2 of the drawings, there is shown a personal care absorbent article 10 including a body side liner material or cover 12 according to the present invention. As shown in the drawings, the personal care absorbent article is in the form of a sanitary napkin. This, however, should not be construed as a limitation as to the type of personal care absorbent article or the particular end use to which the combination film and nonwoven material of the present invention can be applied.

The sanitary napkin 10 includes a body side liner or cover 12, a back side liner or baffle 14 and an absorbent core 16 disposed between the body side liner 12 and the back side liner 14. Both the body side liner 12 and the back side liner 14 are joined to one another about their peripheries 17 so as to create an envelope which houses the absorbent core 16. In more refined embodiments of the sanitary napkin 10, the absorbent core 16 can include a top layer 18 positioned adjacent the body side liner 12 and a bottom layer 20 positioned adjacent the back side liner 14.

In order to protect against unwanted leakage, the back side liner or baffle 14 is typically constructed from a liquid impermeable material such as a plastic film or a film/nonwoven composite or laminate. If desired, a breathable film material can be used for construction of the baffle 14 so that the sanitary napkin can pass water vapor.

The body side liner 12 according to the present invention is made from a combination film and lofty nonwoven material including an apertured film layer 22 and a fibrous nonwoven separation layer 26. As can been seen from FIGS. 1 and 2, there are a plurality of apertures 24 extending through the film layer 22 so as to permit fluid flow through the film layer. For purposes of the present invention, "apertures" and "apertured" may include holes and/or slits which create passageways through the film layer from one surface to the other. The apertures may be localized or they may extend across the entire surface of the film layer 22 as shown in FIG. 1. When the aperturing is localized, it will typically be in the form of a longitudinal central portion or strip (not shown) which separates two side portions of the cover which are not apertured (also not shown). In this configuration the entire layer can be made from a film or the longitudinal central portion can be made from an apertured film and the side portions can be made from another material such as a fibrous nonwoven web.

Suitable polymers from which to form the film layer 22 include any material which can be formed into a film including, but not limited to, polyolefins and polyacrylates, as well as copolymers and blends thereof. Specific polymers include, but are not limited to, polyethylene (PE), low density polyethylene (LDPE), linear low density polyethylene (LLDPE) and ethylene vinyl acetate (EVA).

There are a number of well known means for forming such films including, but not limited, casting and blowing. Typically the film layer will have a thickness between about 0.025 and about 1.0 millimeters and a percent open area due to the aperturing of between about 10 and about 30% based upon the surface area of the film layer 22. Percent open area is calculated by specifying a unit area, calculating the surface area of all open areas within the specified unit area, dividing this total open area by the total surface area within the specified unit area and then multiplying the quotient by 100 to yield percent open area. The size and number of apertures can be varied depending upon the viscosity and other properties of the body fluid being transported through the film layer 22. The film may be hydrophilic or hydrophobic or it may be treated to be such. Many film extrusion blends will have a slip agent such as a fatty ester added to the blend which also makes an otherwise hydrophobic film more hydrophilic.

Suitable apertured films include AET polyethylene CKX 215 film made by Applied Extrusion Technology of Middleton, Del.; SULTEX PF-10 EVA/(LDPE/PP)/EVA film from Sultex SRL of Agliana, Italy and a Mitsui low density polyethylene film from Mitsui and Co., Ltd of Tokyo, Japan. The AET polyethylene CKX 215 film has a percent open area of approximately 28%. The SULTEX PF-10 film is a three-layer laminate and has an 18–22% open area. The two outer layers are composed of ethylene vinyl acetate (EVA) and the inner layer is a mixture of 17% polypropylene and 73% low density polyethylene. The Mitsui low density polyethylene film has a 22–24% open area. The apertures are tapered capillaries which extend from the bottom side of the film layer.

To insure adequate protection against leakage, the film layer 22 and the baffle 14 are bonded to one another about their peripheries 17. The two materials may be joined to one another by any suitable means which will provide an appropriate seal. If the materials forming the film layer 22 and the baffle 14 are thermally compatible, the peripheries 17 may be heat sealed to one another. Alternatively, the two layers may be joined using adhesives including water-based, solvent-based and hot-melt adhesives. The peripheral seal 17 is an important feature that provides added protection against leakage.

Disposed below and in direct contact with the apertured film layer 22 is the fibrous nonwoven separation layer 26. The separation layer 26, due to its unique design and interaction with the film layer 22, readily desorbs fluid from the surface of the sanitary napkin and transfers it to the absorbent core 16. To maximize fluid intake and minimize fluid rewet, the separation layer 26 should be made from a lofty fibrous nonwoven web. As is demonstrated by the examples below, the nature of the fibrous nonwoven web is critical to the performance of the combination film and nonwoven material as well as the end product of the present invention. Typically, the support layer 12 will have a caliper between about 0.76 and 3.8 mm, a basis weight of between about 0.5 and 2.5 ounces per square yard (17 gsm and 85 gsm) and an average pore size of between about 100 and about 400 microns.

Any process for forming fibrous nonwoven webs can be used provided the resultant web has the properties described herein. Two particularly well-suited formation processes include spunbonding and through-air bonded carded web forming processes both of which are well known and need not be described herein in detail. Spunbond nonwoven webs are made from fibers which are formed by extruding a molten thermoplastic material as filaments from a plurality of fine, usually circular, capillaries in a spinneret with the diameter of the extruded filaments then being rapidly reduced, for example, by non-eductive or eductive fluid-drawing or other well known spunbonding mechanisms. The production of spunbonded nonwoven webs is illustrated in patents such as Appel, et al., U.S. Pat. No. 4,340,563, Dorschner et al., U.S. Pat. No. 3,692,618; Kinney, U.S. Pat. Nos. 3,338,992 and 3,341,394; Levy, U.S. Pat. No. 3,276,944; Peterson, U.S. Pat. No. 3,502,538; Hartman, U.S. Pat.

No. 3,502,763; Dobo et al., U.S. Pat. No. 3,542,615; and Harmon, Canadian Patent Number 803,714.

A particularly well-suited spunbonded nonwoven web for the separation layer 26 is made from side-by-side polyethylene/polypropylene spunbond bicomponent fibers. The process for forming such fibers and resultant webs includes using a pair of extruders for separately supplying both the polyethylene and the polypropylene to a bicomponent spinneret. Spinnerets for producing bicomponent fibers are well known in the art and thus are not described herein in detail. In general, the spinneret includes a housing containing a spin pack which includes a plurality of plates having a pattern of openings arranged to create flow paths for directing the high melting and low melting polymers to each fiber-forming opening in the spinneret. The spinneret has openings arranged in one or more rows and the openings form a downwardly extending curtain of fibers when the polymers are extruded through the spinneret. As the curtain of fibers exit the spinneret, they are contacted by a quenching gas which at least partially quenches the fibers and develops a latent helical crimp in the extending fibers. Oftentimes the quenching air will be directed substantially perpendicularly to the length of the fibers at a velocity of from about 100 to about 400 feet per minute at a temperature between about 45° and about 90° F.

A fiber draw unit or aspirator is positioned below the quenching gas to receive the quenched fibers. Fiber draw units or units or aspirators for use in meltspinning polymers are well known in the art. Exemplary fiber draw units suitable for use in the process include linear fiber aspirators of the type shown in U.S. Pat. No. 3,802,817 to Matsuki et al. and eductive guns of the type shown in the U.S. Pat. Nos. 3,692,618 to Dorshner et al. and 3,423,266 to Davies et al. The fiber draw unit in general has an elongated passage through which the fibers are drawn by aspirating gas. The aspirating gas may be any gas, such as air that does not adversely interact with the polymers of the fibers. The aspirating gas can be heated as the aspirating gas draws the quenched fibers and heats the fibers to a temperature that is required to activate the latent crimps therein. The temperature required to activate the latent crimping within the fibers will range from about 110° F. to a maximum of less than the melting point of the low melting component polymer which, in this case, is the polyethylene. Generally, a higher air temperature produces a higher number of crimps.

The drawn and crimped fibers are deposited onto a continuous forming surface in a random manner, generally assisted by a vacuum device placed underneath the forming surface. The purpose of the vacuum is to eliminate the undesirable scattering of the fibers and to guide the fibers onto the forming surface to form a uniform unbonded web of bicomponent fibers. If desired, the resultant web can be lightly compressed by a compression roller before the web is subjected to a bonding process.

To bond the bicomponent spunbonded web a through-air bonder is used. Such through-air bonders are well known in the art and therefore need not be described. In the through-air bonder, a flow of heated air is applied through the web to heat the web to a temperature above the melting point of the lower melting point component of the bicomponent fibers but below the melting point of the higher melting point component. Upon heating, the lower melting polymer portion of the web fibers are melted and the melted portions of the fibers adhere to adjacent fibers at the cross-over points while the high melting polymer portions of the fibers tend to maintain the physical and dimensional integrity of the web.

Bonded carded webs are made from staple fibers which are usually purchased in bales. The bales are placed in a picker which separates the fibers. Next, the fibers are sent through a combing or carding unit which further breaks apart and aligns the staple fibers in the machine direction so as to form a machine direction-oriented fibrous nonwoven web. Once the web has been formed, it is then bonded by one or more of several bonding methods. One bonding method is powder bonding wherein a powdered adhesive is distributed through the web and then activated, usually by heating the web and adhesive with hot air. Another bonding method is pattern bonding wherein heated calendar rolls or ultrasonic bonding equipment is used to bond the fibers together, usually in a localized bond pattern though the web can be bonded across its entire surface if so desired. The best method though, when using bicomponent staple fibers is to use a through-air bonder such as is described above with respect to the bicomponent spunbond web formation process.

An important factor in forming the separation layer 26 is that it maintains its lofty nature. As a result, bonding processes which unduly compact the fibrous nonwoven web should be avoided. Through-air bonding and adhesive bonding are examples of bonding processes which do not adversely affect the loft of the resultant web. Here again, such bonding processes are well known and need not be described in detail.

Suitable fibers for forming the fibrous nonwoven web will typically include thermoplastic fibers such as those made from polyolefins and polyesters as well as polyolefin copolymers such as polyethylene/polypropylene copolymers. Such fibers are usually well adapted to heat and powder bonding, have good resilience and come in a wide variety of deniers. Suitable fiber deniers will typically range between about 1.5 and 6. Bicomponent fibers are particularly well-suited for use with the present invention. Bicomponent fibers can be staple length fibers or longer more continuous fibers such as are produced in the above-described spunbond process. Bicomponent fibers usually have a lower melting point polymer portion and a higher melting point polymer portion with the lower melting point portion acting as the means for bonding the fibers together once a sufficient degree of heat has been applied to the structure. Such bicomponent fibers can have, for example, side-by-side, sheath/core and islands-in-sea cross-sections. With all such cross-sections, at least a portion of the exterior surface of the bicomponent fiber contains the lower melting point polymer component so that bonding between the fibers can take place.

Two particularly well-suited lofty nonwoven separation layers as described below in the examples are a polyethylene/polypropylene side-by-side bicomponent spunbond nonwoven web using 3 denier fibers and having a basis weight of 1.2 osy (41 gsm) with a bulk of 55–65 mils and a pore size range between about 100 and 120 microns. The second material is a through-air bonded carded staple fiber bicomponent web having a basis weight of 0.8 osy (27 gsm), a bulk of 55 mils and a pore size between about 100 and 150 microns. The web is made from a 50/50 weight percent blend, based upon the total weight of the web, of 1.8 and 3 denier polyethylene sheath/polyester core staple fibers having 38 mm fiber lengths. Generally, however, the separation layer will have a bulk between about 0.76 and 3.8 millimeters, a basis weight of between about 17 and 85 grams per square meter, and an average pore size of between about 100 and 400 microns.

Many of the fibers used to make the separation layer 26 are generally hydrophobic though they do not necessarily need to be so. To aid in the transfer of the fluid from the apertured film layer 22 to the absorbent core 16, it is usually desirable to treat the fibers forming the separation layer 26 with some type of surfactant or wetting agent. Such surfactants and wetting agents are well known and can be added internally during the fiber forming process or as a post-treatment as with a surfactant spray which is sprayed on the fibers and then dried.

It is important that the apertured film layer 22 and the separation layer 26 be in intimate contact with one another at least in the areas of aperturing in the film layer. Due to the interaction between the apertured film layer 22 and the separation layer 26 it is not necessary that the two layers be adhesively or otherwise joined to one another provided there is still intimate contact between the two layers. It is possible, however, to adhere the two layers to one another if so desired through such means as adhesive or heat bonding if the fibers and film are thermally compatible with one another.

To assist in the downward movement of fluid from the body side liner 12 to absorbent core 16, it is generally desirable to create a pore size gradient within the absorbent core 16 wherein the pores adjacent the body side liner are larger in size than the pores adjacent the bottom of the absorbent core. Such pore size gradients increase the capillary suction action of the fluid thereby causing the fluid to be more rapidly drawn into the interior of the sanitary napkin 10 and subsequently retained therein. Consequently, it is desirable that the size of the individual apertures or openings in the film layer be greater than the size of the pores in the separation layer with the size of the pores in the separation layer in turn being larger than the pore size of the absorbent core 16. To further facilitate this capillary suction phenomena, it is possible to create an absorbent core with two or more zones or layers. As shown in FIG. 2, the absorbent core 16 may include a top layer 18 and a bottom layer 20. The top layer 18 and the bottom layer are both made from fiberized wood pulp or fluff with the top or body side layer 18 having a lower density than the bottom or garment facing layer 20. For example, the top layer can have a density between about 0.03 and about 0.10 grams/cc while the bottom layer 20 can have a density of about 0.05 to about 0.15 grams/cc.

To demonstrate the unique functionality of the apertured film and separation layer combination of the present invention and its usefulness in personal care absorbent articles, a series of samples were prepared and then tested. The test procedures, samples and test results are set forth below.

TEST PROCEDURES

To measure how quickly an apertured film and nonwoven laminate would accept a liquid, a penetration rate test was performed using "Z-Date," a synthetic menstrual fluid formulation containing, on a weight percent basis, approximately 82.5% water, 15.8% polyvinyl pyrrolidone and 1.7% salts, coloring agents and surfactants. It has a viscosity of 17 centipoise and a surface tension of 53.5 dynes per centimeter. A 3 inch by 7 inch sample of the test material was insulted on the film side with 10 cc of synthetic menstrual fluid delivered from a fluid reservoir having a 2 inch by 0.5 inch delivery slot. The time to absorb 8 cc of fluid was then measured in seconds. A lower absorption time as measured in seconds was an indication of a faster intake rate for the particular material.

In personal care absorbent article applications, it is desirable that once a liquid such as menses has passed through the body side liner, the liquid should not rewet the surface or at least rewet the surface as little as possible. To test for the amount of rewet, ten cubic centimeters of the synthetic menstrual fluid were delivered to a fresh test specimen of the same size as described above from a reservoir having a 2 inch by 0.5 inch delivery slot. Next a blotter was placed on top of the specimen and one pound per square inch of pressure was applied for a period of 3 minutes. After the 3 minute interval, the blotter paper was removed and weighed and the amount of synthetic menstrual fluid absorbed by the blotter paper was measured in grams. Higher values were an indication of a greater degree of rewet for the particular material tested.

To measure the Starrett Bulk or bulk of the material which relates to the material's thickness, five inch by five inch (127 millimeter×127 millimeter) samples of material were compressed under a load of 0.05 pounds per square inch and the thickness of the material was measured while the sample was under compression. Higher numbers indicated thicker, more bulky materials.

The pore size of the spaces between the fibers is calculated using the Laplace equation for capillary tension based upon the pore radius:

$$R = -2\alpha \frac{(dynes/cm) \cos \beta}{\delta P \ (dynes/cm^2)}$$

where: $\alpha$ = fluid surface tension
$\beta$ = liquid/solid contact angle
— receding if pores are desorbed
— advancing if pores absorb
$\delta P$ = $\rho g h$ The pore size is thus two times the radius or the calculated diameter of the pore. To obtain an average pore size, five separate pore size readings are performed and the sum of these readings is divided by five to obtain an average.

EXAMPLES

Testing was conducted on a series of apertured film/nonwoven separation layer composites. To demonstrate their properties, they were used as body side liners or covers for two sanitary napkin designs. The first sanitary napkin design was a Kimberly-Clark KOTEX® Maxi Pad currently sold in the United States. The second sanitary napkin was also a Kimberly-Clark product, in this case, the European version of the KOTEX® Maxi Pad. To act as a further reference point, an ALWAYS® sanitary napkin manufactured by the Procter and Gamble Company of Cincinnati, Ohio was also tested.

The U.S. version of the KOTEX® Maxi Pad sanitary napkin consisted of a body side liner, an absorbent core and a plastic film baffle. The absorbent core was a multicomponent structure. The portion of the absorbent core closest to the body side liner comprised six plies of creped tissue body wadding, each of which weighed 19 gsm. Below this portion of the absorbent core there was a single layer of 19 gsm tissue which surrounded a 6.86 gram fluff batt having a density of 0.07 grams/cc. Forming the body side liner was a polypropylene spunbond web which was wrapped around the entire structure. The spunbond web was point bonded with 15% bond area and treated with Triton® X-102 nonionic surfactant from Union Carbide of Sisterville, Va. at an add-on level of approximately 0.26% by weight based upon the weight of the cover material.

The European version of the KOTEX® Maxi Pad sanitary napkin had a transfer layer was made from meltblown material at a basis weight of 45 gsm.

The other control sanitary napkin was an ALWAYS® sanitary napkin from the Procter and Gamble Company of Cincinnati, Ohio. It had a peripheral seal construction with an apertured film body side liner and no transfer layer.

Three commercially available films were selected for use with the present invention. They included the previously described Sultex film from Gruppo Fintex and Partners Italia of Pistoia, Italy, the AET film from Applied Extrusion Technologies of Middleton, Del. and the Mitsui film from Mitsui and Company, Ltd. of Tokyo, Japan.

In conjunction with the above mentioned films, a series of fibrous nonwoven web separation layers were prepared and tested. One set of separation layers were made from bicomponent spunbond nonwoven webs while a second set of separation layers were made from through-air bonded carded webs using polyethylene sheath/polypropylene core bicomponent staple fibers. In addition, several standard fibrous nonwoven webs were also prepared including a spunbond and a meltblown web to demonstrate the difference between the materials of the present invention and conventional two layer cover materials.

The bicomponent spunbond nonwoven web (Bico SB) was made with 3 denier polyethylene/polypropylene spunbond fibers. The web had a basis weight of 1.2 osy (41 gsm), a bulk of 0.052 inches (1.2 mm) and an average pore size of 140 microns. The through-air bonded carded web (TABCW) had a basis weight of 0.8 osy (27 gsm) and was made from a 50/50 weight percent blend, based upon the total weight of the web, of 51 mm long 1.8 and 3.0 denier polyethylene sheath/polyester core bicomponent staple fibers. The comparative spunbond nonwoven web was made from 5.0 denier polypropylene fibers. It was point bonded using a point bond pattern having a total bond area of 15%. The spunbond web had a basis weight of 0.95 osy (32.3 gsm), a bulk of 0.011 inches (2.8 mm) and an average pore size of 85 microns. The comparative meltblown web was made from polypropylene fibers with deniers less than one. The resultant web had a basis weight of 1.3 osy (44.5 gsm). It was point bonded with a total bond area of 15%. All of the fibers in the above-described webs were treated with a surfactant.

As indicated by the examples below, various combinations of the above-described materials were prepared and then placed on top of the aforementioned standard sanitary napkins chassis and subsequently tested. The combinations and test results are set forth below.

EXAMPLE 1

In Example 1 three sanitary napkins were tested for penetration time and rewet properties in accordance with the test procedures set forth above using synthetic menstrual fluid. Sample 1a was a Sultex film placed on top of but not glued to a KOTEX® Maxi Pad chassis (U.S. version). The original nonwoven cover on the KOTEX® Maxi Pad was removed and the Sultex film was used in its place. Sample 1b used the same KOTEX® Maxi Pad chassis with a combination Sultex film and a 1.2 osy (41 gsm) through-air bonded bicomponent spunbond web separation layer made from 3 denier polyethylene/polypropylene side-by-side fibers. The Sultex film and bicomponent spunbond web separation layer were sequentially placed on top of the KOTEX® Maxi Pad chassis with the bicomponent spunbond web adjacent the absorbent core. There was no gluing between the film and the nonwoven layer or between the nonwoven layer and the absorbent core. Sample 1c was a Procter and Gamble ALWAYS® Dri-Weave® sanitary napkin. The test results for penetration time and rewet are shown in Table I.

TABLE I

| SAMPLE | NAPKIN DESIGN | COVER | PENETRATION RATE (sec) | REWET (gms) |
|---|---|---|---|---|
| 1a | KOTEX® Maxi-Pad | Sultex Film | 17 | 1.0 |
| 1b | KOTEX® Maxi-Pad | Sultex Film/ Bico SB NW | 12 | 0.1 |
| 1c | ALWAYS® Sanitary Napkin | Apertured Film | 8 | 0.2 |

As can be seen from Table I, the ALWAYS® sanitary napkin had the best penetration rate with 8 seconds. The KOTEX® Maxi Pad with the Sultex film only (Sample 1a) had a penetration rate which was nearly double that of Sample 1c, however, when the Sultex film was modified by the addition of a bicomponent spunbond nonwoven web separation layer (Sample 1b), the penetration rate dropped a full 5 seconds. In addition, the amount of rewet for Sample 1b dropped by a factor of 10 and was half that of Sample 1c. As a result, it can be seen that the addition of the bicomponent spunbond fibrous nonwoven web separation layer greatly enhanced the penetration rate and rewet properties of the film layer only cover material when used in conjunction with a sanitary napkin.

EXAMPLE 2

In Example 2, eleven samples were prepared (Samples 2a–2k). The samples included covers made from the previously described Sultex, Mitsui and AET films alone and in combination with the previously described 1.2 osy (41 gsm) bicomponent spunbond (Bico SB) separation layer and a 0.8 osy (27 gsm) through-air bonded carded web (TABCW) separation layers according to the present invention. All cover materials were placed on top of a KOTEX® Maxi Pad chassis (U.S. version) which had the original cover removed. Again, the film and film/nonwoven layers were not glued to the absorbent core and the film and nonwoven layers were not glued to themselves. The samples were tested for penetration and rewet properties using synthetic menstrual fluid and the results are set forth in Table II below. In addition, penetration rates and rewet properties were also determined for cover materials which comprised only the bicomponent spunbond separation layer (Sample 2j) and the through-air bonded carded web separation layer (Sample 2k) according to the present invention.

TABLE II

| SAMPLE | COVER | PENETRATION RATE (sec) | REWET (gms) |
|---|---|---|---|
| 2a | Sultex | 18.85 | 0.97 |
| 2b | Sultex W/Bico SB | 11.70 | 0.03 |
| 2c | Sultex W/TABCW | 9.12 | 0.04 |
| 2d | Mitsui | 15.68 | 0.04 |
| 2e | Mitsui W/Bico SB | 9.70 | 0.02 |
| 2f | Mitsui W/TABCW | 8.30 | 0.03 |
| 2g | AET Film | 21.55 | 1.28 |
| 2h | AET Film W/Bico SB | 11.55 | 0.07 |
| 2i | AET Film W/TABCW | 7.98 | 0.08 |
| 2j | Bico SB Alone | 12.36 | 0.10 |
| 2k | TABCW Alone | 7.24 | 0.30 |

As can be seen from Table II, in all instances, the penetration times for the apertured films were reduced when used in conjunction with either the bicomponent spunbond (Bico SB) separation layer (Samples 2b, 2e and 2h) or the bicomponent through-air bonded carded web (TABCW) separation layer (Samples 2c, 2f and 2i). The amount of rewet was reduced in all cases as well. In comparing Sample 2a and 2b, the amount of rewet was reduced by a factor of 32 and by a factor of 24 with respect to Samples 2a and 2c. With Samples 2h and 2i the rewet value of Sample 2g was reduced respectively by a factor of 18 and 16.

EXAMPLE 3

Having demonstrated in the previous two examples that improved penetration rates and rewet properties are achievable with the present invention when compared to conventional nonwoven covers and film covers alone, in example 3 the materials of the present invention were tested against two regular transfer layer materials. Pieces of spunbond (SB) material and meltblown (MB) material have been used in the past to separate nonwoven covers on personal care absorbent articles from the absorbent cores. Two such materials were prepared and placed under a Sultex film and the composite was then placed on top of a Kotex® Maxi Pad (European version) and tested for penetration time and rewet. These samples were then compared to Kotex® Maxi Pad chassis (European version) covered with the Sultex film/nonwoven combinations according to the present invention as described in Example 2. See Table III below.

TABLE III

SULTEX FILM W/TRANSFER LAYER VARIATIONS

| SAMPLE | COVER MATERIAL | PENETRATION TIME(sec) | REWET (grams) |
|---|---|---|---|
| 3a | Sultex Film | 13.34 | 1.00 |
| 3b | Sultex/Bico SB | 11.50 | 0.10 |
| 3c | Sultex/TABCW | 10.17 | 0.05 |
| 3d | Sultex/SB | 20.79 | 0.38 |
| 3e | Sultex/MB | 20.89 | 0.24 |

As can be seen from the data in Table III above, the samples with conventional nonwoven layers (Sample 3d and 3e) had penetration rates which were essentially double that of the feminine pads using the material of the present invention (Samples 3b and 3c). They were also higher than the penetration rate for the Sultex film alone (Sample 3a). The spunbond nonwoven layer in Sample 3d used 5 denier polypropylene fibers, had a basis weight of 0.95 osy (32.3 gsm) and was point bonded with a bond pattern having a percent bond area of 15%. This nonwoven layer did not have the properties including loftiness necessary to provide the attributes of the present invention. The meltblown nonwoven layer in Sample 3e had a basis weight of 1.3 osy (44.5 gsm), an average pore size of 30 microns and a fiber size of less than 1 denier, all of which combined to form a material did not provide the fast penetration rates and low rewet values which were possible with the material of the present invention.

Having thus described the invention in detail, it should be apparent that various modifications and changes can be made in the present invention without departing from the spirit and scope of the following claims.

What is claimed is:

1. A body side liner for personal care absorbent articles comprising:

an apertured film layer superimposed and in contact with a separation layer, said film layer defining apertures therein, said film layer having a percent open area of between about 10 and 30 percent based upon the surface area of said film, said separation layer comprising a fibrous nonwoven web having a bulk of between about 0.76 and 3.8 millimeters, a basis weight of between about 17 and 85 grams per square meter and an average pore size of between about 100 and 400 microns, said apertured film layer and said separation layer when used as a body side liner for a personal care absorbent article yielding a penetration rate of 12 seconds or less and a rewet which does not exceed 0.1 grams.

2. The body side liner of claim 1 wherein said fibrous nonwoven web contains a plurality of bicomponent fibers.

3. The body side liner of claim 2 wherein said bicomponent fibers are side-by-side fibers which contain polyethylene and polypropylene.

4. The body side liner of claim 3 wherein said fibers have a fiber denier between about 1.5 and 6.

5. The body side liner of claim 2 wherein said bicomponent fibers are side-by-side fibers which contain polyethylene and polyester.

6. The body side liner of claim 5 wherein said fibers have a fiber denier between about 1.5 and 6.

7. A personal care absorbent article comprising:

a body side liner and a back side liner with an absorbent core disposed therebetween, said body side liner comprising an apertured film layer superimposed and in contact with a separation layer, said separation layer being positioned between said film layer and said absorbent core, said film layer defining apertures therein, said film layer having a percent open area of between about 10 and 30 percent, said separation layer comprising a fibrous nonwoven web having a bulk of between about 0.76 and 3.8 millimeters, a basis weight of between about 17 and 85 grams per square meter and an average pore size of between about 100 and 400 microns, said apertured film layer and said separation layer when used as a body side liner for a personal care absorbent article yielding a penetration rate of 12 seconds or less and a rewet which does not exceed 0.1 grams.

8. The personal care absorbent article of claim 7 wherein said absorbent core includes a first layer positioned toward said body side liner and a second layer positioned toward said back side liner.

9. The personal care absorbent article of claim 8 wherein said absorbent core comprises fiberized wood pulp, said first layer having a density of about 0.03 to about 0.10 grams per cubic centimeter and said second layer having a density of about 0.05 to about 0.15 grams per cubic centimeter.

10. The personal care absorbent article of claim 7 wherein said fibrous nonwoven web includes a plurality of bicomponent fibers.

11. The personal care absorbent article of claim 10 wherein said bicomponent fibers have a side-by-side configuration.

12. The personal care absorbent article of claim 11 wherein said bicomponent fibers are made from polypropylene and polyethylene.

13. The personal care absorbent article of claim 10 wherein said bicomponent fibers have a sheath/core configuration.

14. The personal care absorbent article of claim 13 wherein said bicomponent fibers are made from polyethylene and polyester.

15. The personal care absorbent article of claim 7 wherein said body side liner has a body side liner periphery and said back side liner has a back side liner periphery, said body side liner periphery and said back side liner periphery being joined together.

16. The personal care absorbent article of claim 7 wherein said body side liner includes side portions separated by a longitudinal central portion, said longitudinal central portion comprising said apertured film and said side portions comprising a fibrous nonwoven web.

17. The personal care absorbent article of claim 7 wherein said personal care absorbent article is a sanitary napkin.

* * * * *

UNITED STATES PATENT AND TRADEMARK OFFICE
CERTIFICATE OF CORRECTION

PATENT NO. : 5,643,240
DATED : July 1, 1997
INVENTOR(S) : Jackson et al.

It is certified that error appears in the above-identified patent and that said Letters Patent is hereby corrected as shown below:

Title page, item [73], "Neenan" should read --Neenah--;
Column 5, line 27, "units or units or aspirators" should read --units or aspirators--;
Column 8, line 66, "layer was" should read --layer which was--;
Column 9, line 35, "(2.8 mm)" should read --(0.28 mm)--.

Signed and Sealed this

Ninth Day of June, 1998

BRUCE LEHMAN

*Attest:*

*Attesting Officer*    *Commissioner of Patents and Trademarks*